United States Patent [19]

Yang et al.

[11] Patent Number: 5,208,379
[45] Date of Patent: May 4, 1993

[54] HYDROLYSIS OF POLYURETHANES

[75] Inventors: Lau S. Yang, Wilmington, Del.; Diane A. Macarevich, Collegeville, Pa.

[73] Assignee: Arco Chemical Technology, L.P., Wilmington, Del.

[21] Appl. No.: 882,776

[22] Filed: May 14, 1992

[51] Int. Cl.$^5$ .......................................... C07C 209/44
[52] U.S. Cl. ..................... 564/468; 564/330; 564/331; 564/334; 564/393; 564/305; 564/437; 564/461; 564/498; 564/505; 564/511; 564/512; 568/613; 568/617; 568/621; 568/623; 568/624
[58] Field of Search ............. 564/468, 305, 330, 331, 564/334, 393, 437, 461, 498, 505, 511, 512; 568/613, 617, 621, 623, 624

[56] References Cited

U.S. PATENT DOCUMENTS

| | | | |
|---|---|---|---|
| 3,266,927 | 8/1966 | Lorenz et al. | 117/98 |
| 3,404,103 | 10/1968 | Matsudaira | 260/2.3 |
| 3,441,616 | 4/1969 | Pizzini et al. | 260/615 |
| 3,738,946 | 6/1973 | Frulla et al. | 260/2.3 |
| 3,978,128 | 8/1976 | Meluch et al. | 260/570 D |
| 4,039,568 | 8/1977 | Sakai et al. | 260/453 P |
| 4,162,995 | 7/1979 | Sheratte | 260/2.3 |
| 4,196,148 | 4/1980 | Mahoney | 260/582 |
| 4,281,197 | 7/1981 | Oblinger | 564/393 |
| 4,328,368 | 5/1982 | Salloum et al. | 564/393 |
| 4,339,358 | 7/1982 | Schütz | 521/49.5 |
| 4,399,236 | 8/1983 | Niederdellmann et al. | 521/49 |

OTHER PUBLICATIONS

Chem. Abst., 101: 8661r (Jpn. Kokai JP 59-21, 715) (1984).
Chem. Abst. 102: 150807g (Gawish et al.).
Am. Dyest. Rep. 32(12), 37 (1984).

Primary Examiner—Richard L. Raymond
Assistant Examiner—Scott Rand
Attorney, Agent, or Firm—Stephen D. Harper

[57] ABSTRACT

Waste or scrap polyurethane may be conveniently and economically converted to useful active-hydrogen containing polyethers and polyamines by contacting the polyurethane with water, strong base, and an activating agent such as a quaternary ammonium compound containing at least 15 carbon atoms or an organic sulfonate containing at least 7 carbon atoms. The activating agent helps to accelerate the rate of base catalyzed hydrolysis.

22 Claims, No Drawings

HYDROLYSIS OF POLYURETHANES

FIELD OF THE INVENTION

The present invention relates to an improved process for the treatment of polyether-based polyurethane reaction products whereby the active hydrogen-containing polyethers utilized in preparing the polyurethanes are recovered in high yield under relatively mild hydrolysis conditions. The process also produces polyamines corresponding in structure to the polyisocyanates employed in preparing the polyurethanes. More specifically, the invention pertains to methods for the base-catalyzed hydrolysis of polyurethanes wherein the reaction rate is accelerated by the presence of an activating agent such as a quaternary ammonium salt or an organic sulfonate.

BACKGROUND OF THE INVENTION

Polyurethanes are materials of considerable utility in the production of rigid and flexible foams, solid and microcellular elastomers, sealants, coatings, and adhesives. The versatility, relatively low cost, and superior properties of polyurethanes have resulted in the rapid growth of the polyurethane industry over the past 50 years. Currently, many millions of pounds of polyurethanes are produced each year throughout the world. Unfortunately, most polyurethanes are thermoset materials which are cross-linked to one degree or another. Unlike thermoplastics such as polyethylene, polypropylene, and polystyrene, scrap or waste polyurethanes thus cannot be readily remelted or reprocessed into useful articles. Since it would be hi9highly desirable for economic and environmental reasons to reuse or recover the large volume of scrap or waste polyurethane generated each year rather than burning it or disposing of it in landfills, considerable inventive effort has been devoted to devising processes for recovering useful chemical components from scrap polyurethane materials.

Hydrolysis of a polyurethane using base catalysis so as to recover polyether polyols and polyamines is known in the art, but suffers from several disadvantages. At relatively low temperatures, the hydrolysis rate is slow. At higher temperatures, the rate is faster but certain undesired side reactions may occur. The amount of base (caustic)required is also high relative to the amount of polyurethane being treated, making the process economically unattractive.

The present invention overcomes the aforementioned deficiencies of prior art hydrolytic recovery methods by providing a process which accomplishes effective and selective hydrolysis of a polyurethane to active hydrogen-containing polyethers and polyamines using lower temperatures, lower levels of basic catalyst, and/or shorter treatment times.

SUMMARY OF THE INVENTION

This invention furnishes a method of hydrolyzing a polyurethane produced by reacting a active hydrogen-containing polyether and an organic polyisocyanate which comprises contacting said polyurethane with water in the presence of an effective amount of a strong base selected from the group consisting of alkali metal oxides, alkali metal hydroxides, alkaline earth metal oxides, and alkaline earth metal hydroxides and an effective amount of an activating agent selected from the group consisting of quaternary ammonium salts containing at least 15 carbon atoms and organic sulfonates containing at least 7 carbon atoms for a time and at a temperature effective to yield the active hydrogen-containing polyether and an organic polyamine.

DETAILED DESCRIPTION OF THE INVENTION

The polyurethanes which may be subjected to the process of the present invention are those prepared from active hydrogen-containing polyethers and polyisocyanates. Polyurethanes of this type are well known and are described, for example, in Ulrich, "Urethane Polymers", in *Encyclopedia of Chemical Technoloqy*, Vol. 23, pp. 576–608(1983) and Backus et al., "Polyurethanes", in *Encyclopedia of Polymer Science and Technology*, Vol. 13, pp. 243–303(1988). The active hydrogen-containing polyether is typically a polyether polyol (i.e., a polyether having terminal hydroxyl groups) but may also be an amine-functionalized polyether (e.g., the "Jeffamine" polyoxypropylamines sold by Texaco Chemical Co.). The polyether is characterized by having an equivalent weight of at least 200 and repeating oxyalkylene units in its polymeric backbone. Such materials are generally made by the catalytic ring-opening polymerization of one or more cyclic ethers such as epoxides, oxetanes, or oxolanes. Initiators having two or more active hydrogens such as polyhydric alcohols, amines, or acids may be employed to vary the functionality (number of active hydrogens) of the polyether. If more than one type of cyclic ether is used, they may be reacted either simultaneously (to yield a random-type copolymer) or sequentially (to yield a block-type copolymer). Illustrative cyclic ethers include propylene oxide, ethylene oxide, butylene oxide, tetrahydrofuran, and oxetane. Examples of suitable active hydrogen-containing polyethers include polypropylene glycol, polyethylene glycol, polytetramethylene glycol, polytrimethylene glycol, ethylene oxide-capped polypropylene glycol, random copolymers of ethylene oxide and propylene oxide, and the like.

The polyurethane employed in the process of this invention may be derived from any polyisocyanate reactant (i.e., an organic compound containing two or more isocyanate groups). Suitable polyisocyanates include, but are not limited to, aliphatic diisocyanates, cycloaliphatic diisocyanates, aryl alkyl diisocyanates, aromatic diisocyanates (e.g., toluene diisocyanates and diisocyanatodiphenyl methanes), aromatic triisocyanates, as well as isocyanate mixtures such as the isocyanates commonly referred to as "PMDI". Modified, masked, or blocked polyisocyanates may, of course, also be utilized.

The waste or scrap polyurethane product to be treated may also include any of the conventional additional reactants or additives known in the art such as chain extenders or curatives (relatively low molecular weight active hydrogen-containing compounds such as glycols and di- or polyamines), surfactants, fillers, stabilizers, anti-oxidants, colorants, polymers other than the polyurethane polymer (e.g., styrene-acrylonitrile copolymers such as are found in polymer polyols), urethane-promoting catalysts, and the like. The polyurethane may be in solid, microcellular, or foam form and may range from a rubbery, elastomeric material to a hard, rigid substance. To facilitate handling of the polyurethane, it is generally desirable to chop, pulverize, grind, or otherwise comminute the polyurethane such that it is in the form of relatively small particles or granules (i.e., less than about 1" in average diameter). If the polyurethane is a foam, it may be partially or fully compressed prior to contacting with the water, strong base, and activating agent. If the polyurethane is in solid form, an initial pulverization step is highly advantageous so as to maximize the surface area available for reaction (thereby reducing the reaction time required to achieve the desired level of hydrolysis).

The process of this invention will result in the effective hydrolytic cleavage of the urethane and urea bonds present in the polyurethane being treated so as to generate active hydrogen-containing polyethers, polyamines, and, if the polyurethane was prepared using chain extenders or curatives, low molecular weight glycols, diols, diamines, and the like.

While the strong base used may be any base having a high $pk_b$ value, the strong base is most preferably an alkali metal hydroxide (e.g., sodium hydroxide, potassium hydroxide), an alkali metal oxide (e.g., potassium oxide, sodium oxide), an alkaline earth metal hydroxide (e.g., calcium hydroxide, magnesium hydroxide, barium hydroxide), an alkaline earth metal oxide (e.g., calcium oxide, magnesium oxide, barium oxide), or a mixture thereof. While the amount of base is not critical, the concentration in the reaction mixture must be sufficient to catalyze the desired hydrolysis of the polyurethane at a practicable rate. The optimum amount of base will thus be dependent upon the reaction temperature and activating agent concentration, among other factors, but typically will be from about 0.1 to 25 weight percent based on the weight of polyurethane.

For reasons that are not well understood, the addition of certain substances to a polyurethane/strong base/water reaction mixture has been found to greatly enhance the rate at which the polyurethane is converted by hydrolysis to active hydrogen-containing polyethers and organic polyamines. These substances, which are herein generically referred to as "activating agents", may be either quaternary ammonium salts, organic sulfonates, or some combination or mixture thereof. Although the addition of even trace amounts of these activating agents will accelerate the hydrolysis rate, it is preferred that at least 0.05 parts by weight activating agent per 100 parts by weight polyurethane be used. For reasons of economy the maximum amount of activating agent present will generally be 5 parts by weight per 100 parts polyurethane. All other factors being equal, the hydrolysis rate will typically increase as the concentration of activating agent is increased.

The quaternary ammonium salts useful in the invention include those organic nitrogen-containing compounds in which the molecular structure includes a central positively-changed nitrogen atom joined to four organic (i.e., hydrocarbyl) groups or incorporated into a pyridinium ring and a negatively charged anion such as halide, hydrogen sulfate, carboxylate or hydroxide. Such compounds have been recognized by the prior art to be useful as surface-active agents, phase transfer agents, biocides, antistatic additives, and the like, but their ability to function as effective activating agents in the base-catalyzed hydrolysis of polyurethanes has hitherto been unappreciated. Quaternary ammonium salts are well known and are described, for example, in Cahn et al., "Surfactants and Defensive Systems", in *Encyclopedia of Chemical Technology*, Third Edition Vol. 22, pp. 383-385 (1983) and *Catonic Surfactants*, E. Jungermann, Ed., Marcel Dekker, New York (1970), pp. 1-173. Many such compounds are commercially available at relatively low cost.

Quaternary ammonium salts containing a total of at least 15 carbon atoms have been found to be most effective in increasing the rate of polyurethane hydrolysis in the presence of strong base. In general, it is preferred that each of the R groups is alkyl rather than aryl or arylalkyl.

Particularly preferred quaternary ammonium salts include those substances having the general structure.

wherein $R_1, R_2, R_3$, and $R_4$ are the same or different and are hydrocarbyl groups selected from alkyl (a paraffinic hydrocarbon group derived from an alkane by removal of one hydrogen from the alkane), aryl (an aromatic hydrocarbon group having the ring structure characteristic of benzene, naphthalene and the like), and arylalkyl (an alkyl group substituted with an aryl group) and X is halide (e.g., chloride, bromide), hydrogen sulfate, carboxylate (e.g. acetate) or hydroxide.

In a preferred embodiment, $R_1$ is an arylalkyl group such as benzyl and $R_2, R_3$, and $R_4$ are each a $C_4$-$C_{12}$ linear, branched, or cyclic alkyl group such as butyl, pentyl, hexyl, heptyl, cyclohexyl, octyl, nonyl, decyl, dodecyl, or a branched or substituted isomer thereof. Illustrative examples of quaternary ammonium salts of this type include benzyltributyl ammonium chloride, benzyltributyl ammonium bromide, benzyltributyl ammonium hydrogen sulfate, benzyl tributyl ammonium hydroxide, benzyl trioctyl ammonium chloride, and the like.

In another preferred embodiment, $R_1, R_2, R_3$, and $R_4$ are each a $C_4$-$C_{12}$ alkyl group as in tetrabutyl ammonium hydrogen sulfate, tetraoctyl ammonium bromide, and the like.

In yet another preferred embodiment, $R_1$ and $R_2$ are each a $C_8$-$C_{24}$ alkyl group and $R_3$ and $R_4$ are methyl. The $R_1$ and $R_2$ groups are suitably derived from fatty acids or mixtures of fatty acids. Dialkyl dimethyl ammonium salts of this class are available commercially and include "Adrogen 432 CG" (a quaternary ammonium salt produced by Sherex Chemical Co. wherein $R_1, R_2$ are $C_{12}$-$C_{18}$ alkyl groups and X is chloride), "Arguad 2C-75" (a quaternary ammonium salt produced by Sherex Chemical Co. wherein $R_1$ and $R_2$ are alkyl groups derived from coconut fatty acids and X is chloride), "Varisoft 137" (a quaternary ammonium salt produced by Sherex Chemical Co. wherein $R_1$ and $R_2$ are alkyl groups derived from hydrogenated tallow fatty acids and X is $CH_3SO_4$), and "Kemaine Q2802C" (a quaternary ammonium salt produced by Witco Chemical Corp. wherein $R_1$ and $R_2$ are $C_{22}$ alkyl groups and X is chloride).

Yet another embodiment of the invention employs alkyl benzyl quaternary ammonium salts (benzalkonium salts) wherein $R_1$ is benzyl, $R_2$ is a $C_8$-$C_{24}$ alkyl group (preferably derived from a fatty acid), and $R_3$ and $R_4$ are methyl. Examples of this type of activating agent include, but are not limited to, "Barquat MB-50" (a quaternary ammonium salt produced by Lonza, Inc. wherein $R_2$ is myristyl and X is chloride), "Stedbac" (a quaternary ammonium salt produced by Hexcel Corp. wherein $R_2$ is stearyl and X is chloride), and "BTC 50" (a quaternary ammonium salt produced by Onyx Chemical Corp. wherein $R_2$ is a $C_{12}, C_{14}, C_{16},$ or $C_{18}$ alkyl group and X is chloride).

Alkyltrimethyl ammonium salts wherein $R_1$ is a $C_8$–$C_{24}$ alkyl group (preferably derived from a fatty acid) and $R_2$, $R_3$, and $R_4$ are methyl are also suitable for use in the process of the invention. Example of such compounds include "Acetoquat CTAB" (a quaternary ammonium salt produced by Aceto Chemical Co. wherein $R_1$ is cetyl and X is bromide).

Alkyl pyridinium salts corresponding to the following general structure may also be utilized as activating agents:

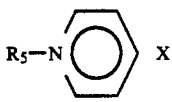

$R_5$ is preferably a long chain $C_8$–$C_{24}$ alkyl group (e.g., cetyl, lauryl), while X can be any of the anions identified hereinabove. Such alkyl pyridinium salts are commercially available and include, for example, "Dehyquart C" (a quaternary ammonium salt produced by Henkel Corp. wherein $R_5$ is lauryl and X is chloride).

Other illustrative quaternary ammonium salts appropriate for use as the activating agent in the process of this invention include benzyltriphenyl phosphonium chloride, octyltriethyl ammonium bromide, decyltriethyl ammonium bromide, dodecyltriethyl ammonium bromide, trioctylmethyl ammonium chloride, and tricaprylyl methyl ammonium chloride (available commercially as "Aliquat 336" from General Mills) The quaternary ammonium salt activating agent may be generated in situ during the hydrolysis by the addition of precursor components (e.g., tertiary amines and alkylating agents) to the reaction mixture.

The other class of activating agents useful in the practice of this invention includes organic sulfonates (i.e., organic compounds containing at least one sulfonate functional group). Such substances have the general formula

wherein R is a linear, branched, cyclic saturated or unsaturated alkyl group, an aryl group, or alkyl aryl group containing at least 7 carbon atoms and M is alkali metal (e.g., sodium, potassium), alkaline earth metal (e.g., calcium, barium, magnesium), or ammonium ($NH_4$, $NHR_3$, $NH_2R_2$, $NH_3R$, where M may also be hydrogen provided sufficient strong base is present during the hydrolysis reaction to convert the organic sulfonate into its salt (anionic) form and R is an organic moiety such as methyl or ethyl). These compounds are known to be useful surface active agents, coupling agents, solubilizers, hydrotropes, dispersants, and stabilizers, but have not heretofore been proposed as activating agents in combination with strong base for the purpose of promoting a polyurethane hydrolysis process. Organic sulfonates are described in Cahn et al., "Surfactants and Detersive Systems", in *Encyclopedia of Chemical Technology*, Vol. 22, pp. 347–360(1983) and McCutcheon, *Synthetic Detergents*, (1950) pp. 120–151.

One type of organic sulfonate especially suitable for use is an alkylaryl sulfonate having the general structure

wherein R is a $C_1$–$C_{15}$ alkyl group (linear, branched, or cyclic) and M is alkaline earth metal, alkali metal, or ammonium. Representative commercially available examples of such organic sulfonates include "Conco AAS-60S" (produced by Continental Chemical Co.; R is dodecyl and M is triethanolammonium), "Conoco C-650" (produced by Conoco Inc.; R is tridecyl and M is sodium), "Emkal NOBS" (produced by Emkay Chemical Co., R is nonyl and M is sodium), and "Witconate PI059" (produced by Witco Chemical Corp.; R is dodecyl and M is $NH_4$). Both linear alkylate sulfonates and branched alkylate sulfonates are particularly preferred for use, especially dodecyl benzene sulfonates. The salts of toluene-, xylene-, and isopropylbenzene sulfonic acid may also be employed.

Also useful are alpha-olefin sulfonates (also referred to as "AOS") having the general structure

wherein $R_2$ is a $C_8$–$C_{15}$ alkyl group and M is alkali metal, alkaline earth metal, or ammonium. "Witconate AOS" (produced by Witco Chemical Corp.) is one example of such an alpha-olefin sulfonate wherein R is a mixture of $C_{10}$–$C_{12}$ alkyl groups and M is sodium. Commercial AOS is often a multicomponent mixture in which the double bond may be located at a number of positions along the chain and which may contain significant proportions of hydroxyalkane sulfonate isomers.

Naphthalene sulfonates are also suitable activating agents for use in the polyurethane hydrolysis process of this invention. These materials are manufactured by sulfonation and neutralization of naphthalene, tetrahydronapthalene, alkyl naphthalenes, formaldehyde-naphthalene condensation products, and similar compounds derived from naphthalene or substituted naphthalenes. The naphthalene sulfonates may be alkali metal, alkaline earth metal, or ammonium salts. An example of a suitable naphthalene sulfonate is "Emkal NNS" (produced by Emkay Chemical Co.), having the formula $RC_{10}H_6SO_3Na$ wherein R is nonyl.

Other suitable organic sulfonates include petroleum sulfonates, which are produced by reaction of high boiling petroleum feedstocks such as white oil or lubestocks with oleum and neutralization with alkali metal or the like. Petroleum sulfonates are available commercially from Exxon, Shell, Stephan, and Witco.

If the hydrolysis reaction temperature selected is relatively high, it will generally be desirable to use an organic sulfonate rather than a quaternary ammonium salt as the activating agent as the former compounds tend to have a higher stability at elevated temperatures.

The exact temperature at which the polyurethane is contacted with water, the strong base, and the activating agent is not critical, but should be sufficiently high that the desired rate of hydrolysis is achieved. Temperatures of from 80° C. to 225° C. have been found to be effective in accomplishing a high degree of polyurethane conversion within a practicably short period of time (typically, 5 minutes to 12 hours).

While water functions as a reactant in the desired polyurethane hydrolysis reaction and thus does not need to be present in stoichiometric excess relative to the urethane functional groups in the polymer to be hydrolyzed, it will generally be desirable to utilize a substantial quantity of water in order that it may conveniently serve as a reaction medium and solvent or carrier for the strong base and activating agent. For these reasons, the water is preferably present in condensed (liquid) form. Typically, the weight ratio of polyurethane to water is from 3:1 to 1:15. The hydrolysis is generally conducted at atmospheric pressure, although superatmospheric pressures may be employed, if desired. Optionally, a water-miscible or water-immiscible solvent such as alcohol, ketone, ester, ether, amide, sulfoxide, halogenated hydrocarbon, aliphatic hydrocarbon, or aromatic hydrocarbon may be present in the reaction mixture to facilitate the hydrolysis process or to aid in recovering the reaction products.

The hydrolysis reaction may be carried out in a batch, continuous, or semi-continuous manner in any appropriate vessel or other apparatus (for example, a stirred tank reactor or screw extruder) whereby the polyurethane may be contacted with water in the presence of the strong base and activating agent. It will generally be preferred to agitate or stir the reaction components so as to assure intimate contact, rapid hydrolysis rates, and adequate temperature control. The active hydrogen-containing polyethers, organic polyamines, chain extenders, and curatives produced in the hydrolysis may be separated and recovered from the crude reaction mixture using any suitable method or combination of methods known in the art such as extraction (using water-immisible organic solvents as the extractant, for example), distillation, precipitation, filtration and the like. The recovered active hydrogen-containing polyether may be reused in the preparation of new polyurethane materials. The recovered polyamines can be converted to organic polyisocyanates by conventional processes and similarly employed as components of polyurethanes.

Without further elaboration, it is believed that one skilled in the art can, using the preceding description, utilize the present invention of its fullest extent. The following examples, therefore, are to be considered as merely illustrative and not limitative of the claims or remainder of the disclosure in any.

EXAMPLE 1

A 300 mL citrate bottle was charged with 5N sodium hydroxide solution (50 mL), a water-blown slabstock flexible polyurethane foam (50g; the foam was first compressed in a 150° C. press for 5-10 minutes before being cut into 1/2"×1" pieces), and tetrabutyl ammonium hydrogen sulfate (0.5g). The bottle was sealed with a crown cap and placed in a constant temperature oil bath at 150° C. for 8 hours. After cooling, the bottle was opened and the contents poured into a volumetric flask. Sufficient tetrahydrofuran (ca. 400 mL) was added to bring the total volume to 500 mL. After thoroughly mixing, 15 mL of the liquid sample was transferred to a centrifuge tube and centrifuged to remove a small amount of insoluble material. The clear supernatant was decanted and the residual solids washed again with fresh tetrahydrofuran and centrifuged. The supernatants were combined and the solvent removed by evaporation. The weight of non-volatiles obtained represented about 90-95% of the original weight of the polyurethane foam after allowing for the sample volume actually employed.

The above hydrolysis procedure was repeated, but the crude reaction product obtained was treated in the following manner to separate and characterize the hydrolysis products. The crude product was poured from the citrate bottle to a round bottom flask and the water removed using a rotary evaporator. The residue was extracted with hexane (500 mL), the hexane solution thus obtained being washed with dilute hydrochloric acid to remove a small amount of amine which was present. The solvent was then evaporated to yield a pale yellow liquid having a viscosity of 500 cps at room temperature and a hydroxyl number of 65 mgKOH/gram. A yield of 31g was obtained, corresponding to 95% of the polyether polyol used originally in preparing the polyurethane foam. Infrared spectroscopy and gel permeation chromatography confirmed that the product was a 3000 molecular weight polyether polyol.

The residue remaining after the hexane extraction was placed in a small flask and distilled under vacuum (18mm Hg; 150° C) to give a pale yellow solid. This solid was determined by gas chromatography to be an 80/20 mixture of 2,4- and 2,6- toluene diamine. The solid was obtained in 50% yield (8.5g) based on the amount of toluene diisocyanate incorporated in the original polyurethane foam. Higher yields (85%) were obtained when the experiment was repeated on a larger (2X) scale.

EXAMPLES 2-4

To demonstrate the effect of activating agent concentration on the rate of polyurethane hydrolysis, Example 1 was repeated using varying amounts of tetrabutyl ammonium hydrogen sulfate. As shown in Table I, high yields of THF-soluble products were obtained among either 0.5 or 1.0 parts by weight activating agent per 100 parts by weight polyurethane. However, a poor yield was observed in the absence of the tetrabutyl ammonium hydrogen sulfate (Comparative Example 2).

TABLE I

| Example No. | Activating Agent, g | Soluble product, g | Yield, % |
|---|---|---|---|
| 2* | 0 | 22 | 45 |
| 3 | 0.25 | 40 | 80 |
| 4 | 0.50 | 45 | 90 |

*comparative example

From these examples, it is clear that the activating agent significantly improves the efficiency of the polyurethane hydrolysis. The crude products obtained in Example 3 and 4 were easily processed fluids whereas the crude product of Comparative Example 2 was semisolid and contained large pieces of unreacted foam.

EXAMPLES 5-7

These examples show that the weight ratio of polyurethane to water is not critical to the successful operation of the process. Example 1 was repeated using 1 weight percent tetrabutyl ammonium hydrogen sulfate (based on the weight of foam) and varying quantities of foam (Table II). High yields of THF-soluble product were obtained in each case, even with relatively high polyurethane to water ratios.

TABLE II

| Example No. | Wt. Foam, g | Soluble Product, % Yield |
|---|---|---|
| 5 | 15 | 95 |
| 6 | 25 | 93 |
| 7 | 50 | 93 |

EXAMPLES 8-16

These examples illustrate the use of different type of activating agents on the process of the invention (Table III). The procedure of Example 1 was repeated using 1 weight percent of each activating agent (based of weight of foam).

TABLE III

| Example No. | Activating Agent | Soluble Product, % Yield |
|---|---|---|
| 8* | None | 50 |
| 9 | tetrabutylammonium hydrogensulfate | |
| 10 | benzyltributyl ammonium chloride | 87 |
| 11* | diazabicyclooctane | 69 |
| 12 | sodium dodecyl benzene sulfonate | 63 |
| 13* | 18-crown-6 | 59 |
| 14* | "Igepal 890" (an ethoxylated non-ionic produced by GAF, Corp.) | 54 |
| 15* | benzyltriethyl ammonium chloride | 49 |
| 16 | naphthalene formaldehyde sulfonate ("Tamol N", a product of Rohm & Haas) | 71 |

*comparative example

Interestingly, the amine which was tested (diazabicyclooctane) did not perform as well as the quaternary ammonium salts tested in Example 9 and 10. Although crown ethers are generally considered to be good phase transfer agents, the yield obtained using 18- crown-6 in comparative Example 13 was only slightly better than the control example (Example 8) where no activating agent was present. Similarly, little or no enhancement in hydrolysis rate was observed using a non-ionic surfactant (Comparative Example 14) or a quaternary ammonium salt containing only 13 carbon atoms (Comparative Example 15). Improved yields of THF-soluble hydrolysis products were realized using high carbon-content quaternary ammonium salts (Example 9 and 10) and organic sulfonates (Example 12 and 16) as the activating agent.

EXAMPLES 17-19

These examples demonstrate the influence of reaction temperatures on the rate of polyurethane hydrolysis. The procedure of Example 1 was followed using 1 weight percent tetrabutyl ammonium hydrogen sulfate and varying oil bath temperatures (Table IV). The highest yield of THF-soluble product after 8 hours was obtained at 150° C. Only partial hydrolysis of the foam was achieved at 120° C, making quantitative measurement of the amount of the THF-soluble product difficult. More complete hydrolysis at 120° C may be readily accomplished by increasing the reaction time or increasing the strong base and/or activating agent concentrations.

TABLE IV

| Example No. | Temp., °C. | Soluble Product, % Yield |
|---|---|---|
| 17 | 150 | 90 |
| 18 | 140 | 70 |
| 19 | 120 | partial hydrolysis |

EXAMPLES 20-22

The effect of reaction time on polyurethane conversion was studied by repeating the procedure of Example 1 using 1 weight percent tetrabutyl ammonium hydrogensulfate and reaction times of 2, 4, or 8 hours at 150° C. (Table V). High yields of THF-soluble product were obtained even when the reaction time was relatively short, demonstrating the enhancement in hydrolysis rate resulting from the presence of the activating agent.

TABLE V

| Example No. | Time, hr. | Soluble Product, % Yield |
|---|---|---|
| 20 | 8 | 95 |
| 21 | 4 | 90 |
| 22 | 2 | 70 |

EXAMPLE 23

The successful hydrolysis of a high resilience polyurethane foam made from a styrene-acrylonitrile based polymer polyol (6% polymer solids) is demonstrated by this example. The foam was pre-compressed and then contacted with aqueous sodium hydroxide and 1 weight percent tetrabutyl ammonium hydrogen sulfate for 8 hours at 150° C. as described in Example 1. The weight of the THF-soluble product recovered was 93% of the weight of the original foam. An 87% yield of the polyether product was obtained by extracting with cyclohexane.

EXAMPLES 24-26

The procedure of Example 23 was repeated, but using varying concentrations of the activating agent (Table VI). The results show that high yields of hydrolysis products from HR polyurethane foam are only obtained when an activating agent is employed in accordance with this invention.

TABLE VI

| Example No. | Conc. of Activating Agent, % | Soluble Product, % Yield |
|---|---|---|
| 24 | 1 | 90 |
| 25 | 0.5 | 80 |
| 26* | 0 | 60 |

*comparative example

EXAMPLES 27-281

To show that the polyurethane: water ratio and amount of strong base utilized is not critical to the successful operation of the process of this invention, the procedure of Example 23 was repeated using different amounts of 5N sodium hydroxide solution and HR foam (Table VII).

TABLE VII

| Example No. | Polyurethane, g | Caustic, mL | Soluble Product, % Yield |
|---|---|---|---|
| 27 | 25 | 50 | 89 |
| 28 | 50 | 50 | 92 |

EXAMPLE 29

This example demonstrates the operation of the process at a higher reaction temperature and lower strong base concentration. At 1.7 weight percent sodium hydroxide (based on the weight of polyurethane foam), hydrolysis of a polyurethane foam was essentially quantitative after 6 hours at 195° C. (operating pressure ca. 300 psig).

We claim:

1. A method of hydrolyzing a polyurethane produced by reacting an active hydrogen containing polyether and an organic polyisocyanate which comprises contacting said polyurethane with water in the presence of an effective amount of a strong base selected from the group consisting of alkali metal oxides, alkali metal hydroxides, alkaline earth metal oxides, and alkaline earth metal hydroxides and an effective amount of an activating agent selected from the group consisting of quaternary ammonium salts containing at least 15 carbon atoms and organic sulfonates containing at least 7 carbon atoms for a time and at a temperature effective to yield the active hydrogen-containing polyether and an organic polyamine.

2. The method of claim 1 wherein the strong base is an alkali metal hydroxide selected from potassium hydroxide and sodium hydroxide.

3. The method of claim 1 wherein the activating agent is a quaternary ammonium salt having the general structure $R_1R_2R_3R_4NX$ wherein $R_1$, $R_2$, $R_4$ and $R_4$ are the same or different and are hydrocarbyl groups selected from alkyl, aryl, and arylalkyl and X is halide, hydrogen sulfate or hydroxide.

4. The method of claim 1 wherein the activating agent is an organic sulfonate selected from the group consisting of alkyl aryl sulfonates, alpha-olefin sulfonates, petroleum sulfonates and naphthalene sulfonates.

5. The method of claim 1 comprising the additional steps of separating and recovering the organic polyamine and active hydrogen-containing polyether.

6. The method of claim 1 wherein the polyurethane is foamed.

7. The method of claim 1 wherein the temperature is from 80° C. to 225° C.

8. The method of claim 1 wherein the amount of strong base is from about 0.1 to 25 weight percent based on the weight of polyurethane.

9. The method of claim 1 wherein the amount of activating agent is from 0.05 to 5 weight percent based on the weight of polyurethane.

10. The method of claim 1 wherein the time is from 5 minutes to 12 hours.

11. The method of claim 1 wherein the weight ratio of polyurethane to water is from 3:1 to 1:15.

12. The method of claim 1 wherein the active hydrogen containing polyether is comprised of oxypropylene repeating units.

13. A method of hydrolyzing a polyurethane foam produced by reacting an-active hydrogen-containing polyether comprised of oxypropylene units and an organic polyisocyanate which comprises:

a) contacting 100 parts by weight of said polyurethane foam with water in the presence of 0.1 to 25 parts by weight of an alkali metal hydroxide and from 0.05 to 5 parts by weight of an organic sulfonate selected from the group consisting of alkyl aryl sulfonates, alpha-olefin sulfonates, petroleum sulfonates, and naphthalene sulfonates at a temperature of from 80° C. to 225° C. for a time effective to yield the active hydrogen-containing polyether and an organic polyamine; and b) separating and recovering the active hydrogen-containing polyether and organic polyamine.

14. The method of claim 13 wherein the organic sulfonate is an alkyl aryl sulfonate having the general structure $$RC_6H_4SO_3M$$

wherein R is a $C_1$–$C_{15}$ alkyl group, M is alkaline earth metal, alkali metal, or ammonium.

15. The method of claim 13 wherein the organic sulfonate is an alpha-olefin sulfonate having the general structure $$R\ CH=CHSO_3M$$

wherein R is a $C_8$–$C_{15}$ alkyl group and M is alkali metal alkaline earth metal, or ammonium.

16. The method of claim 13 wherein the organic sulfonate is a naphthalene sulfonate obtained by sulfonation and neutralization of naphthalene, an alkylnaphthalene, tetrahydronaphthalene, or a formaldehyde-naphthalene condensation product.

17. A method of hydrolyzing a polyurethane foam produced by reacting an active hydrogen-containing polyether comprised of oxypropylene repeating units and an organic polyisocyanate which comprises:

a) contacting 100 parts by weight of said polyurethane foam with water in the presence of 0.1 to 25 parts by weight of an alkali metal hydroxide and from 0.05 to 5 parts by weight of a quaternary ammonium salt containing at least 15 carbon atoms and having the general structure $$R_1R_2R_3R_4NX$$

wherein $R_1$, $R_2$, $R_3$, and $R_4$ are the same or different and are hydrocarbyl groups selected from alkyl, aryl, and arylalkyl and X is halide, hydrogen sulfate, or hydroxide at a temperature of from 80° C. to 225° C. for a time effective to yield the active hydrogen-containing polyether and an organic polyamine; and b) separating and recovering the active hydrogencontaining polyether and organic polyamine.

18. The method of claim 17 wherein R is benzyl and $R_2$, $R_3$, and $R_4$ are each a $C_4$–$C_{12}$ alkyl group.

19. The method of claim 17 wherein $R_1$, $R_2$, $R_3$, and $R_4$, are each a $C_4$–$C_{12}$ alkyl group.

20. The method of claim 17 wherein $R_1$ and $R_2$ are each a $C_8$–$C_{24}$ alkyl group and $R_3$ and $R_4$ are methyl.

21. The method of claim 17 wherein R is benzyl, $R_2$ is a $C_8$–$C_{24}$ alkyl group, and $R_3$ and $R_4$ are methyl.

22. The method of claim 17 wherein $R_1$ is a $C_8$–$C_{24}$ alkyl group and $R_2$, $R_3$, and $R_4$ are methyl.

* * * * *